United States Patent
Takahashi et al.

(10) Patent No.: US 6,784,315 B2
(45) Date of Patent: Aug. 31, 2004

(54) STILBENE DERIVATIVE CRYSTAL AND METHOD FOR PRODUCING THE SAME

(75) Inventors: Shinichiro Takahashi, Kawasaki (JP); Yoko Sugawara, Sagamihara (JP); Hiroyuki Matsueda, Kawasaki (JP)

(73) Assignee: Ajinomoto Co. Inc., Tokyo (JP)

( * ) Notice: Subject to any disclaimer, the term of this patent is extended or adjusted under 35 U.S.C. 154(b) by 0 days.

(21) Appl. No.: 10/243,649

(22) Filed: Sep. 16, 2002

(65) Prior Publication Data

US 2003/0065035 A1 Apr. 3, 2003

Related U.S. Application Data

(63) Continuation of application No. PCT/JP01/02028, filed on Mar. 14, 2001.

(30) Foreign Application Priority Data

Mar. 17, 2000 (JP) ........................................ 2000-076887

(51) Int. Cl.[7] ..................... C07C 233/05; C07C 231/24; A61K 31/16
(52) U.S. Cl. ........................ 564/193; 564/194; 514/626
(58) Field of Search ................................ 564/193, 194; 514/626

(56) References Cited

U.S. PATENT DOCUMENTS 5,674,906 A 10/1997 Hatanaka et al.

OTHER PUBLICATIONS

K. Ohsumi, et al., *Anti–Cancer Drug Design*, vol. 14, pp. 539–548, 1999.

*Primary Examiner*—Shailendra Kumar
(74) *Attorney, Agent, or Firm*—Oblon, Spivak, McClelland, Maier & Neustadt, P.C.

(57) ABSTRACT

A Type IV crystal of (Z)-N-[2-methoxy-5-[2-(3,4,5-trimethoxyphenyl)vinyl]phenyl]-L-serinamide hydrochloride, which can be produced by crystallization using a solvent containing water at 2% by weight at the maximum and which has a X ray powder diffraction pattern containing peaks at least at 13.4°, 18.7°, 19.4°, and 22.5° (2θ), is provided. This compound is useful as an effective ingredient for a carcinostatic agent. The crystal of the present invention has excellent properties desirable from the standpoint of the production of medicinal products, i.e., reduced water adsorption and extremely high stability to water. Also provided are a method for producing the Type IV crystal thereof and a method for use of the crystal.

20 Claims, 4 Drawing Sheets

STILBENE DERIVATIVE CRYSTAL AND METHOD FOR PRODUCING THE SAME

CROSS-REFERENCE TO RELATED APPLICATIONS

This application is a continuation of International Application PCT/JP01/02028, filed on Mar. 14, 2001, and claims priority to Japanese Patent Application No. 2000-076887, filed on Mar. 17, 2000, both of which are incorporated herein by reference in their entireties.

BACKGROUND OF THE INVENTION

1. Field of the Invention

The present invention relates to novel stilbene derivative crystals. More specifically, the invention relates to a novel crystal form of (Z)-N-[2-methoxy-5-[2-(3,4,5-trimethoxyphenyl)vinyl]phenyl]-L-serinamide hydrochloride, which is useful as an effective ingredient of a carcinostatic agent (anticancer agent), methods for producing the same, and the use thereof.

2. Discussion of the Background

Stilbene derivatives of a specific structure exhibit anticancer activity (action), and are useful compounds as effective ingredients of carcinostatic agents (see Japanese Patent Kokai Publication JP-A-8-301831, International Publication WO 99/51246, both of which are incorporated herein by reference in their entireties, and the like).

SUMMARY OF THE INVENTION (Z)-N-[2-methoxy-5-[2-(3,4,5-trimethoxyphenyl)vinyl]phenyl]-L-serinamide hydrochloride represented by the following structure (structural) formula (1):

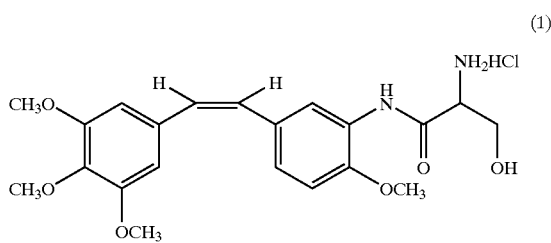

(1)

is particularly excellent as an effective component (ingredient) for the development of a pharmaceutical agent among a great number of stilbene derivatives with a carcinostatic activity. However, the inventors have found that the crystals of this compound as recovered by a general method (hereinafter, the crystal type or form recovered by the general method is referred to as "Type I", and the crystals of this type is referred to as "Type I crystals") adsorbs water (water vapor) to a degree roughly (approximately) proportional to the water vapor pressure (relative humidity), i.e., the Type I crystals adsorb water depending on the surrounding humidity. The inventors have also found that the quantity of the adsorbed water by the Type I crystals is fairly large.

Such crystals which are unstable in the presence of water are not preferable for drug preparation. For the production of drugs and dosage forms (pharmaceutical preparations) thereof, a stable crystal which exhibits reduced (very little) water adsorption and less (very little) water (water vapor) adsorption up to around a relative humidity of 80% is preferable.

Accordingly, it is one object of the present invention to provide crystals of the stilbene derivative represented by the structural formula (1), which exhibit an extremely low water (water vapor) adsorption level as described above, namely a crystal form which is stable to water (moisture).

It is another object of the present invention to provide novel method for producing such a crystal.

It is another object of the present invention to provide novel pharmaceutical compositions which comprise such a crystal.

It is another object of the present invention to provide novel method for producing such a pharmaceutical composition.

It is another object of the present invention to provide novel methods of treating cancer by administering such a pharmaceutical composition to a subject in need thereof.

These and other objects, which will become apparent during the following detailed description, have been achieved by the inventors' investigations of crystals of (Z)-N-[2-methoxy-5-[2-(3,4,5-trimethoxyphenyl)vinyl]phenyl]-L-serinamide hydrochloride as represented by the structural formula (1) described above, and their discovery of a novel crystal thereof which is stable to water (moisture) (hereinafter, the crystal form is referred to as "Type IV crystal"), which differs from the crystal type (Type I) obtained by the general method. As specifically shown in the X ray powder diffraction pattern described below, the Type IV crystal obtained in accordance with the present invention is a novel crystal which is different from the crystal type obtained by the general method. The present inventors have found that the novel crystal is so stable to water (moisture) that the crystal adsorbs extremely little water (water vapor) up to around a relative humidity of 80%. The inventors have also found that a trace content of water in a solvent used for the crystal formation (crystallization) thereof is a factor determining such crystal type. Based on these various findings, the present invention has been achieved.

Thus, in a first embodiment, the present invention provides the novel crystal, more specifically, a Type IV crystal of (Z)-N-[2-methoxy-5-[2-(3,4,5-trimethoxyphenyl)vinyl]phenyl]-L-serinamide hydrochloride represented by the structural formula (1), which is a novel crystal (Type IV crystal) differing from that of the crystal recovered (obtained) by the general method, as shown in the X ray powder diffraction pattern, and which has peaks at least at 13.4°, 18.7°, 19.4° and 22.5° (2θ) in the X ray powder diffraction pattern.

In other embodiments, furthermore, the present invention provides the use thereof (application, etc.) and a method for producing the crystal.

More specifically, the present invention encompasses the following embodiments.

(1) The crystal of the present invention described above, having a X ray powder diffraction pattern which contain peaks at least at 11.1°, 13.4°, 14.2°, 18.7°, 19.4°, 22.5° and 23.4° (2θ).

(2) The crystal of the present invention described above and the crystal described above in (1), which adsorbs water (water vapor) at a level of less than 20 ml/g (preferably, less than 15 ml/g or so) at a relative humidity of 80%, on a prepared water (water vapor) adsorption isotherm (isothermal line) (see Mitsuiki et al., *J. Agric. Food Chem.*, vol. 46, No. 9, pages 3528–3534 (1998)).

Here, the water (water vapor) adsorption level represents the water vapor volume occupying one gram crystal (ml/g) at 0° C. and one atmospheric pressure.

Further, preferably, the water (water vapor) adsorption levels at relative humidity of 40, 60 and 80% are less than about 8 ml/g (more preferably, less than about 6 ml/g), less than about 16 ml/g (more preferably, less than about 9 ml/g) and less than about 20 ml/g (more preferably, less than about 15 ml/g), respectively.

Water (water vapor) adsorption isotherms both in adsorption and desorption processes (water vapor adsorption levels measured by the method for measuring water (moisture content) when humidity increases and decreases to dryness) are shown in FIGS. 3 and 4. Preferably, a smaller level of the resulting two levels satisfies the above numerical range.

(3) The crystal of the present invention and the crystals described above in (1) and (2), which can be crystallized using a solvent, which may be a mixed solvent, containing water at 2% by weight at the maximum, preferably a mixed solvent of methanol-isopropyl acetate which contains substantially no water.

(4) A carcinostatic agent (anticancer agent) such as an oral dosage form or a parenteral dosage form (injections, etc.) containing the Type IV crystal described above or being produced by using the Type IV crystal described above (which may contain carrier(s) used in the method for producing a dosage form (a pharmaceutical preparation).

In other words, the present invention encompasses the use of the Type IV crystal as a carcinostatic agent, and a method of use of the Type IV crystal for a carcinostatic effect such as therapeutic treatment, amelioration (improvement), progress prevention, prophylaxis (prevention), etc. of cancer, comprising administration of the crystal to an animal such as a human in need of the carcinostatic effect.

Incidentally, depending on the symptom and the like of the patient or the like, the appropriate dose of the crystal in this case can be easily determined, based on the method for use of routine carcinostatic agents and known methods for use of the carcinostatic agents. The appropriate carrier for use in the production of dosage forms thereof can also be easily determined on the basis of routine pharmacological methods.

(5) A method for producing a crystal of (Z)-N-[2-methoxy-5-[2-(3,4,5-trimethoxyphenyl)vinyl]phenyl]-L-serinamide hydrochloride represented by the structural formula (1) described above containing a crystallization step therefor, in which the crystallization step uses a crystallization solvent containing water in a maximum amount of 2% by weight (an amount of 2% by weight or less) for the crystallization of the Type IV crystal thereof.

The water content of the crystallization solvent, is more preferably a maximum of approximately 1% by weight (approximately 1% by weight or less), and still more preferably at the most approximately 0.5% by weight (approximately 0.5% by weight or less). Most preferably a solvent which contains substantially no water can be used. In the case when a mixture solvent (a mixed solvent) of more than one solvent is used as the crystallization solvent, the entire crystallization solvent (i.e., all of the solvents together) preferably contains such a small amount of water content in total as described above. Accordingly, in the case when a combination of a good solvent(s) and a poor solvent (s) is used for re-precipitation, for example, the whole mixture system of the good solvent(s) and the poor solvent (s) to be used may be adjusted to the low water content described above. Here, a combination of the good solvent(s) and the poor solvent(s) to be used for re-precipitation is also encompassed within the range of the term "mixture solvent" described above, according to the method of the present invention described above.

(6) The method for producing the crystal (Type IV crystal) described above, where the solvent to be used in the crystallization step is a combination (mixture solvent; mixed solvent) of a good solvent(s) and a poor solvent(s) for the compound (1).

(7) The method for producing the crystal (Type IV crystal) described above, where the good solvent(s) includes at least one compound selected from alcohols, chloroform, acetone, and acetonitrile, and the poor solvent(s) includes at least one compound selected from acetate esters (acetic acid esters), ethers, saturated hydrocarbons, and cyclic saturated hydrocarbons.

(8) The method for producing the crystal (Type IV crystal) described above, where the crystallization step is via (through) re-precipitation method.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

In FIGS. 1 and 2 described above, the horizontal axis represents 2θ (degrees) and the vertical axis represents intensity (CPS).

In FIGS. 3 and 4, the vertical axis represents water (water vapor) adsorption level (ml/g) (water vapor volume occupying one gram of crystal at 0° C. and one atmospheric pressure) and the horizontal axis represents relative humidity (%)/100. Furthermore, open circle (○) represents a value when humidity is increased from dryness and solid circle (●) represents a value when humidity is decreased to dryness.

DETAILED DESCRIPTION OF THE PREFERRED EMBODIMENTS

Figure 1:
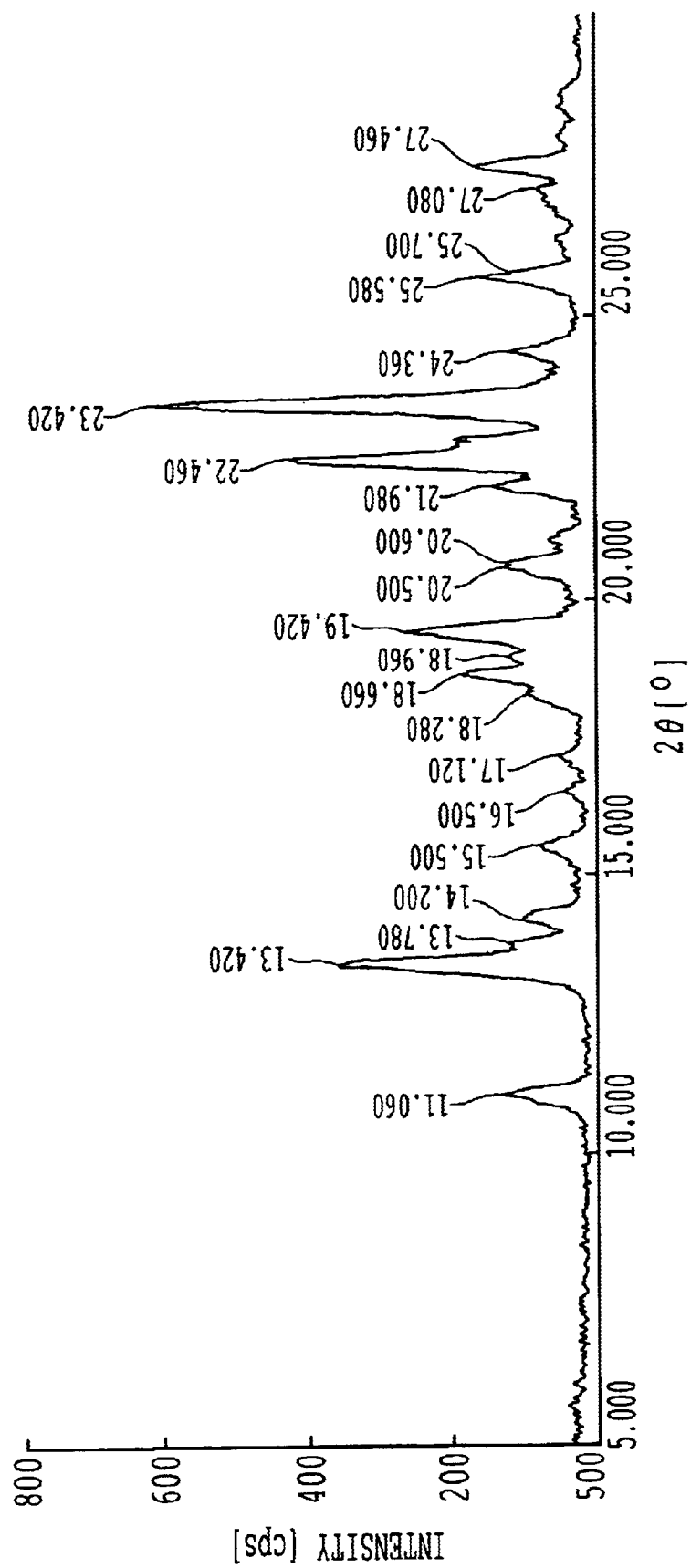
FIG. 1 shows a X ray powder diffraction pattern of the novel Type IV crystal of the present invention, obtained (recovered) in Example 1.

The Type IV crystal of (Z)-N-[2-methoxy-5-[2-(3,4,5-trimethoxyphenyl)vinyl]phenyl]-L-serinamide hydrochloride represented by the structural formula (1) described above in accordance with the present invention can easily be produced via a crystallization step (for example, crystallization, re-precipitation, etc.) using a solvent containing water in a maximum amount of about (approximately) 2% by weight, most preferably a solvent which contains substantially no water, as the crystallization solvent.

The water content is preferably at most about (approximately) 2% by weight, more preferably at most about 1% by weight, and even more preferably at most about 0.5% by weight, based on the total weight of the crystallization solvent to be used (for example, the total weight of good solvent(s) and poor solvent(s) in the case of re-precipitation using a combination of the good solvent(s) to first dissolve the intended compound and the poor solvent (s) to subsequently crystallize the intended compound therefrom, respectively). Most preferably, the crystallization step is carried out, using a solvent which contains substantially no water. Any crystallization step or method can be used with no specific limitation.

Thus, the crystallization step or method includes any crystallization means capable of dissolving the intended compound in a solvent to crystallize the compound, such as concentration crystallization (crystallization under concentration), cooling crystallization (crystallization under cooling), neutralization crystallization (crystallization under neutralization), and crystallization via (through) re-precipitation.

The method for producing the crystal in accordance with the present invention includes a step of crystallizing the Type IV crystal in the hydrochloride form. The Type I crystal obtained (recovered) by the general method can be used simply as the starting material for the crystallization step. However, it is not necessary that the Type I crystal be used as the starting material, provided that the crystallization is performed on the hydrochloride form of the Type IV crystal in the final crystallization step. Therefore, the compound in a form such as the free form or the salt form (which may include the hydrochloride salt form), such as the free form, the salt forms other than hydrochloride salt form, reaction solutions for the synthesis of the intended compound, etc. can be used for the starting material in the crystallization step. Of course, a salt formation step for converting the free form into the hydrochloride salt form is required when using the free form as the starting material. Similarly, a step for converting another salt form(s) into the hydrochloride salt form is required when using such other salt form(s) as the starting material.

Solvents known for use or usable for such organic compound salts can be used as the crystallization solvent. An appropriate crystallization solvent can be selected in a preliminary simple test of solubility for the intended compound. The crystallization solvent for use in this case may be a single solvent or a mixture of more than one solvent (i.e., a mixture solvent; mixed solvent). Preferably, a mixture solvent is used, which is prepared by mixing together a "good" solvent which sufficiently dissolves the intended compound and a "poor" solvent which hardly dissolves the intended compound but which, however, can be dissolved in the good solvent at appropriate volumes. Additionally, a plurality of solvents can be used as the good solvent(s), while a plurality of solvents can be used as the poor solvent(s). In this case, preferably, these plural solvents are miscible together.

For the crystallization via re-precipitation method, the selection of the good solvent(s) and the poor solvent(s) and their volumes thereof are particularly important. However, based on preliminary experiments of solubility therefor and the like, appropriately, the optimal conditions can easily be selected. For example, a combination of methanol and isopropyl acetate is particularly preferable.

Preferred examples of the good solvent include alcohols such as methanol, ethanol, n-propyl alcohol, and isopropyl alcohol; chloroform; acetone; acetonitrile; and the like. Of course, one or more thereof can be used.

Preferred examples of the poor solvent include acetate esters such as methyl acetate, ethyl acetate, isopropyl acetate, n-propyl acetate, n-butyl acetate, and isobutyl acetate; ethers such as diethyl ether; hydrocarbons such as hexane and cyclohexane. Once again, one or more thereof can be used.

Figure 2:
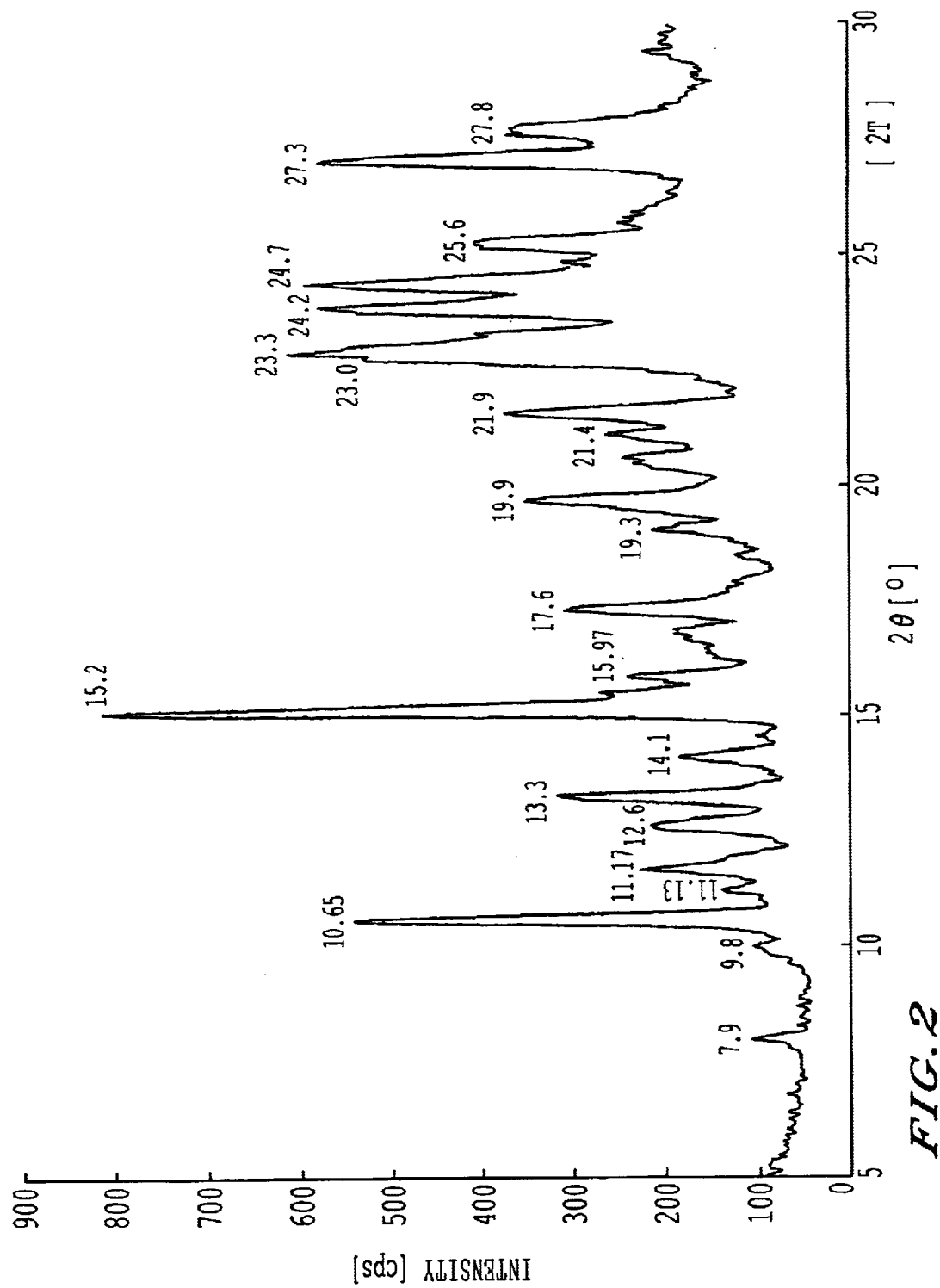
FIG. 2 shows a X ray powder diffraction pattern of the crystal (Type I crystal) obtained by the general method, which is obtained in Comparative Example 1.

The crystal produced in accordance with the present invention (Type IV crystal) distinctly differs from the crystal (Type I crystal) obtained by the general method, in view of the X ray powder diffraction pattern (see FIGS. 1 and 2). In other words, the inventive crystal characteristically exhibits a diffraction pattern which has peaks at least at 13.4°, 18.7°, 19.4°, and 22.5° (2θ), and preferably at 11.1°, 13.4°, 14.2°, 18.7°, 19.4°, 22.5° and 23.4° (2θ).

Figure 3:
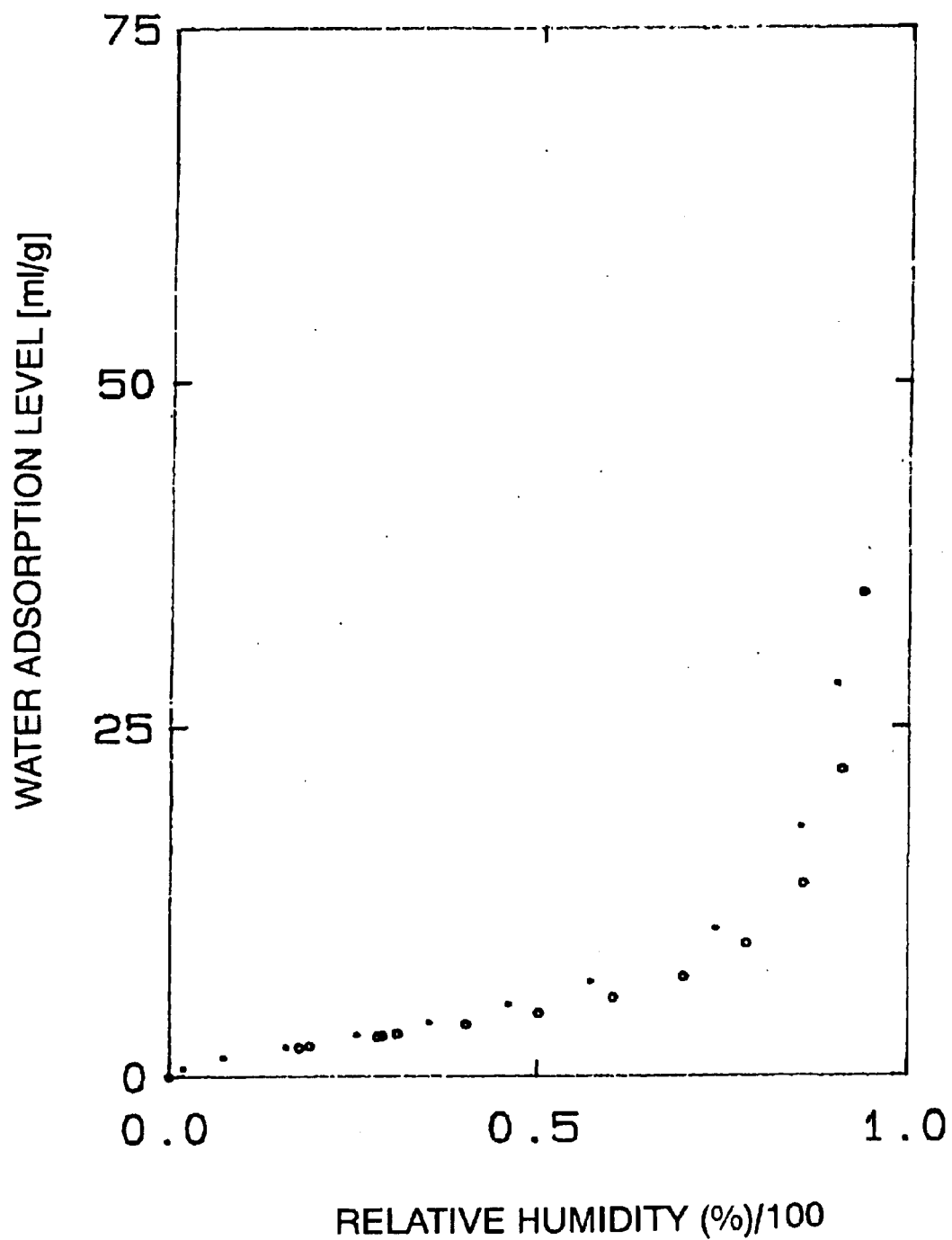
FIG. 3 shows a water (water vapor) adsorption isotherm (isothermal line) of the Type IV crystal of the present invention, obtained in Example 1.
Figure 4:
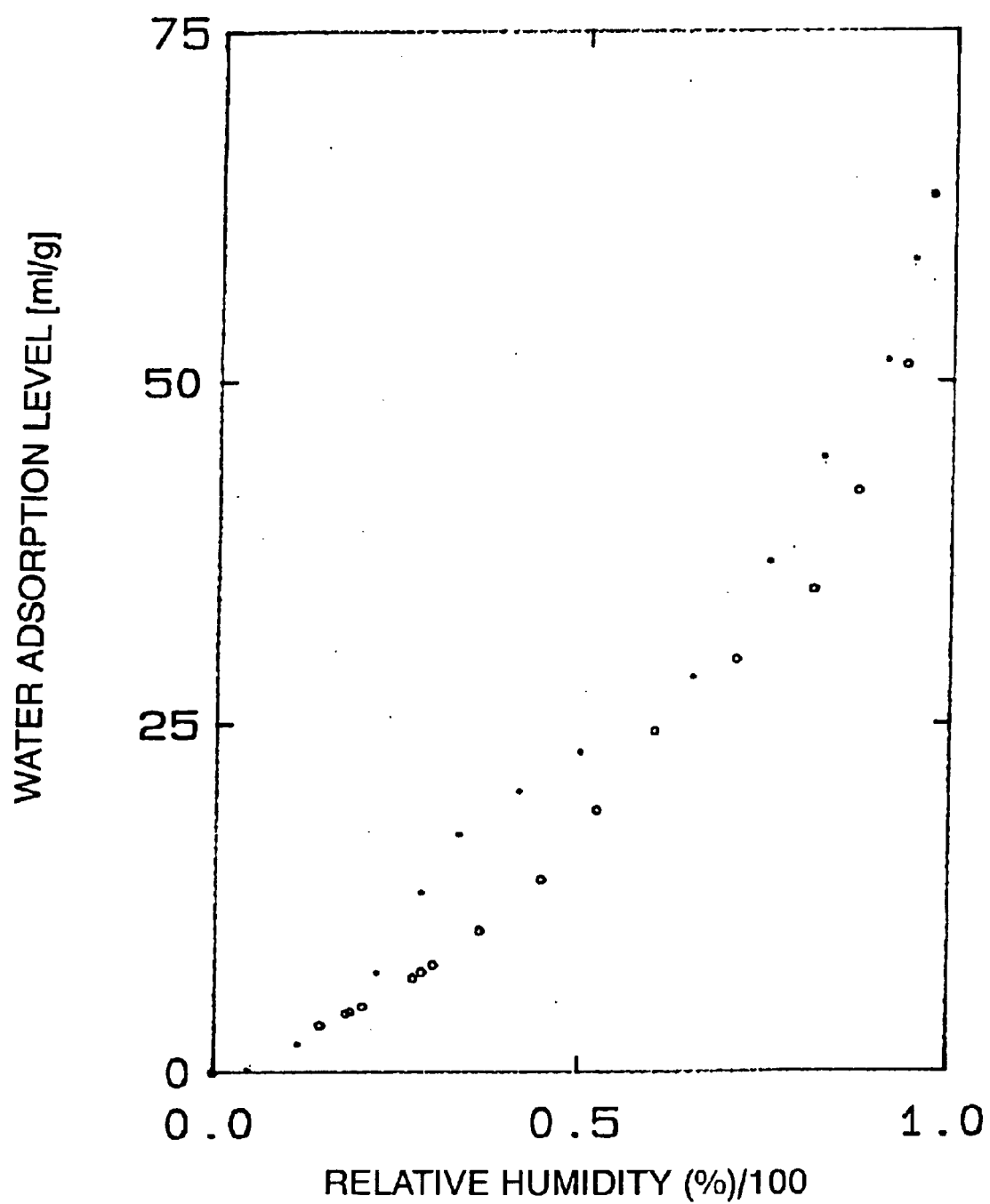
FIG. 4 shows a water (water vapor) adsorption isotherm (isothermal line) of the crystal (Type I crystal) obtained by the general method, which is obtained in Comparative Example 1.

Furthermore, the crystal produced in accordance with the present invention (the inventive product) exhibits a reduced water absorption as compared with the crystal produced by the general method, based on water (water vapor) adsorption isotherm (water adsorption constant temperature line) (see FIGS. 3 and 4). While the Type I crystal of the related art (prior art) adsorbs much water (moisture) in a degree roughly (approximately) proportional to water vapor pressure, the inventive product (Type IV crystal) adsorbs much less water (water vapor) up to around a relative humidity of 80% so that the inventive product is extremely stable to (in the presence of) the water (moisture). Consequently, the inventive product is very useful for the production of drugs and dosage forms (pharmaceutical preparations), compared with the crystal produced by the general method.

The novel crystals of the present invention may be used to prepare pharmaceutical compositions. The formulation of such pharmaceutical compositions may be carried out in the same way as for conventional Type I crystals.

The pharmaceutical compositions which are prepared from the novel crystals of the present invention may be used to treat cancer in the same way that pharmaceutical compositions prepared from conventional Type I crystals are used (see, e.g., U.S. Pat. No. 5,674,906, which is incorporated herein by reference).

EXAMPLES

The present invention will now be described in Examples and a Comparative Example in more detail below. However, these are only typical examples. Thus, the present invention encompasses these Examples but is not limited to these Examples.

Examples and Comparative Example

To an acetonitrile solution of the free-form of the compound of fourmula (1) prepared according to the description of the specification in the Japanese Patent Kokai Publication JP-A-8-301831, Example 4, was added a 10% solution of hydrogen chloride in methanol. The deposited crystals were filtered, recovered, and dried to obtain the crystals (1.2 g) of the stilbene derivative ((Z)-N-[2-methoxy-5-[2-(3,4,5-trimethoxyphenyl)vinyl]phenyl]-L-serinamide 1-hydrochloride salt) as produced by the conversion of the free form into the hydrochloride salt form. The crystals were dissolved in solvents prepared by preliminarily adding water at volumes shown in Table 1 to methanol (anhydrous methanol) (2 ml). Thereafter isopropyl acetate (anhydrous isopropyl acetate) (6 ml) was added at 5° C. to crystallize (re-precipitate) the stilbene derivative, which was then left to stand at 5° C. At 5 minutes and one day after the addition of the isopropyl acetate, the individually separated stilbene derivative crystals were subjected to powder X-ray diffractometry to determine their patterns. The crystals of Examples 1 and 2 showed X ray powder diffraction patterns differing from the pattern of the stilbene derivative crystal (crystal recovered by the general method) used as the starting material in the Examples. The crystal with the X ray powder diffraction pattern of the general crystal recovered by the general method is referred to as a "Type I crystal" (see FIG. 2). The crystal with the novel X ray powder diffraction pattern differing from that of the crystal recovered by the general method is referred to as a "Type IV crystal" (see FIG. 1). These results are shown in Table 1.

TABLE 1

Relation between water content in crystallization solvent and X ray powder diffraction pattern (crystal type)

| Crystallization example | Water (ml) added to methanol (2 ml) | Crystal type | |
|---|---|---|---|
| | | 5 minutes later | 1 day later |
| Example 1 | 0 | IV | IV |
| Example 2 | 0.025 | IV | IV |
| Comparative Example 1 | 0.2 | I | I |

As readily seen from the results, the crystals recovered by reprecipitation after dissolution in 2 ml of methanol with addition of 0.2 ml of water was a Type I crystal with the same X ray powder diffraction pattern as that of the starting material crystal used in the Examples, whereas the crystals recovered by reprecipitation after dissolution in methanol with no water content or with addition of 0.025 ml of water were novel crystals with a X ray powder diffraction pattern never observed for the crystal recovered by the general method (see FIG. 1).

Further, both Types I and IV had an identical melting point by melting point measurement (183 to 186° C.).

As to the water content in entire the crystallization solvent (methanol and isopropyl acetate), still further, it was confirmed that Type IV crystals could be recovered by using a solvent with a water content less than 2% by weight.

Preparation of Water Adsorption Isotherm (Water Adsorption Constant Temperature Line):

After the Type IV crystal recovered above was dried overnight in vacuum at 60° C., the water adsorption level of the crystal was measured at a constant temperature of 25° C. by a fully automatic water adsorption analyzer (BELSORP-18: Nippon Bell K. K.) (see Mitsuiki et al., *J. Agric. Food Chem.*, vol.46, No. 9, pages 3528–3534 (1998)). The results are shown in FIG. 3.

The water adsorption level of the Type I crystal was also measured in the same manner as above. The results are shown in FIG. 4. These results indicate that the Type IV crystal adsorbed much less water up to around a relative humidity of 80%, while the Type I crystal adsorbed water in a degree roughly proportional to relative humidity (water vapor pressure).

Additionally, with respect to the Type IV crystal, the X ray powder diffraction pattern of the Type IV crystal did not change at a relative humidity of 80% or less, involving no crystal structure change, which complies with the water (water vapor) adsorption property of the Type IV crystal.

As readily seen from the aforementioned results, the novel Type IV crystal recovered in accordance with the present invention exhibits excellent water adsorption properties such that the crystal is highly stable to water and is very useful for the production of drugs and dosage forms (pharmaceutical preparations).

Effect of the Invention:

The Type IV crystal form of the stilbene derivative as represented by the structural formula (1) described above in accordance with the present invention is more stable to (in the presence of) water than the crystals (Type I crystal form) recovered by the general method, such that the Type IV crystal adsorbs much less water (water vapor) up to around a relative humidity of 80% and has excellent properties for the production of drugs and dosage forms (pharmaceutical preparations).

By using a crystallization step with a solvent which contains substantially no water, the Type IV crystal with such great properties can be produced easily. Thus, the present invention is highly useful industrially.

What is claimed is:

1. A Type IV crystal of (Z)-N-[2-methoxy-5-[2-(3,4,5-trimethoxyphenyl)vinyl]phenyl]-L-serinamide hydrochloride, which has a X ray powder diffraction pattern which has peaks at least at 13.4°, 18.7°, 19.4°, and 22.5° (2θ).

2. The crystal of claim 1, which has a X ray powder diffraction pattern which has peaks at least at 11.1°, 13.4°, 14.2°, 18.7°, 19.4°, 22.5° and 23.4° (2θ).

3. The crystal of claim 1, which has a water adsorption level less than 20 ml/g at a relative humidity of 80% on a prepared water adsorption isotherm.

4. The crystal of claim 1, which has been crystallized from a solvent, said solvent containing water in an amount of at most 2% by weight.

5. The crystal of claim 4, where said solvent is a mixture of methanol and isopropyl acetate and said solvent contains substantially no water.

6. A pharmaceutical composition, comprising a crystal according to claim 1 or being prepared by using said crystal.

7. The pharmaceutical composition of claim 6, further comprising a pharmaceutically acceptable carrier.

8. The pharmaceutical composition of claim 6, wherein said crystal has a water adsorption level less than 20 ml/g at a relative humidity of 80% on a prepared water adsorption isotherm.

9. The pharmaceutical composition of claim 6, wherein said crystal has been crystallized from a solvent, said solvent containing water in an amount of at most 2% by weight.

10. The pharmaceutical composition of claim 6, where said solvent is a mixture of methanol and isopropyl acetate and said solvent contains substantially no water.

11. A method for producing a crystal of claim 1, comprising crystallizing (Z)-N-[2-methoxy-5-[2-(3,4,5-trimethoxyphenyl)vinyl]phenyl]-L-serinamide hydrochloride from a solvent, wherein said solvent contains water in an amount of at most 2% by weight, based on the weight of said solvent.

12. The method of claim 11, where said solvent is a combination solvent of a good solvent for (Z)-N-[2-methoxy-5-[2-(3,4,5-trimethoxyphenyl)vinyl]phenyl]-L-serinamide hydrochloride and a poor solvent for (Z)-N-[2-methoxy-5-[2-(3,4,5-trimethoxyphenyl)vinyl]phenyl]-L-serinamide hydrochloride.

13. The method of claim 12, where said good solvent is at least one compound selected from the group consisting of alcohols, chloroform, acetone, and acetonitrile; and said poor solvent is at least one compound selected from the group consisting of acetate esters, ethers, saturated hydrocarbons, and cyclic saturated hydrocarbons.

14. The method of claim 11, where said crystallizing comprises re-precipitation.

15. A method for preparing a pharmaceutical composition, comprising mixing a crystal according to claim 1 with a pharmaceutically acceptable carrier.

16. The method of claim 15, wherein said crystal has a X ray powder diffraction pattern which has peaks at least at 11.1°, 13.4°, 14.2°, 18.7°, 19.4°, 22.5° and 23.4° (2θ).

17. The method of claim 15, wherein said crystal has a water adsorption level less than 20 ml/g at a relative humidity of 80% on a prepared water adsorption isotherm.

18. A method of treating cancer, comprising administering an effective amount of a pharmaceutical composition according to claim 6, to a subject in need thereof.

19. The method of claim 18, wherein said pharmaceutical composition further comprising a pharmaceutically acceptable carrier.

20. The method of claim 18, wherein in said pharmaceutical composition, said crystal has a water adsorption level less than 20 ml/g at a relative humidity of 80% on a prepared water adsorption isotherm.

* * * * *